United States Patent [19]

Suthanthiran

[11] Patent Number: 4,834,713
[45] Date of Patent: May 30, 1989

[54] CATHETER BUTTONS

[75] Inventor: Krishnan Suthanthiran, Lorton, Va.

[73] Assignee: Best Industries, Inc., Springfield, Va.

[21] Appl. No.: 114,852

[22] Filed: Oct. 30, 1987

[51] Int. Cl.⁴ .................. A61M 25/02; A61B 19/00
[52] U.S. Cl. ................................. 604/175; 128/899
[58] Field of Search .................... 128/1 R, 899; 604/174–180, 264

[56] References Cited

U.S. PATENT DOCUMENTS

| | | | |
|---|---|---|---|
| 3,402,710 | 9/1968 | Paleschuck | 128/1 R |
| 3,663,965 | 5/1972 | Lee et al. | 604/175 X |
| 4,202,349 | 5/1980 | Jones | 128/1 R |
| 4,271,827 | 6/1981 | Angelchik | 128/1 R |
| 4,360,025 | 11/1982 | Edwards | 604/180 |
| 4,397,641 | 9/1983 | Jacobs | 604/177 |
| 4,534,761 | 8/1985 | Raible | 604/175 |
| 4,563,177 | 1/1986 | Kamen | 604/180 |
| 4,579,120 | 4/1986 | MacGregor | 604/174 X |

FOREIGN PATENT DOCUMENTS 1184139 2/1959 France ........................... 604/174

OTHER PUBLICATIONS

Brachytherapy Update-1986, Hilaris, B. S. and Noni, D., Editors, Memorial Sloan–Kettering Cancer Center, New York, Mar. 22, 1986, p. 153.

Primary Examiner—Dalton L. Truluck
Attorney, Agent, or Firm—Parkhurst, Oliff & Berridge

[57] ABSTRACT

A non-metallic catheter button body having a variety of geometric shapes, having integrally secured therewith a metallic marker element, to anchor a catheter or surgical tube in the body with less pain to the patient while providing an X-ray visible marker, which button substantially reduces loss of the patient's skin from scattered electrons resulting from a bombardment by radiation from radioactive material. The non-metallic button body may further include an integral non-metallic stem portion to facilitate the crimping of the stem, anchoring of tubes in the body, and insertion of ribbons of radioactive material therein.

43 Claims, 6 Drawing Sheets

U.S. Patent  May 30, 1989  Sheet 1 of 6  4,834,713
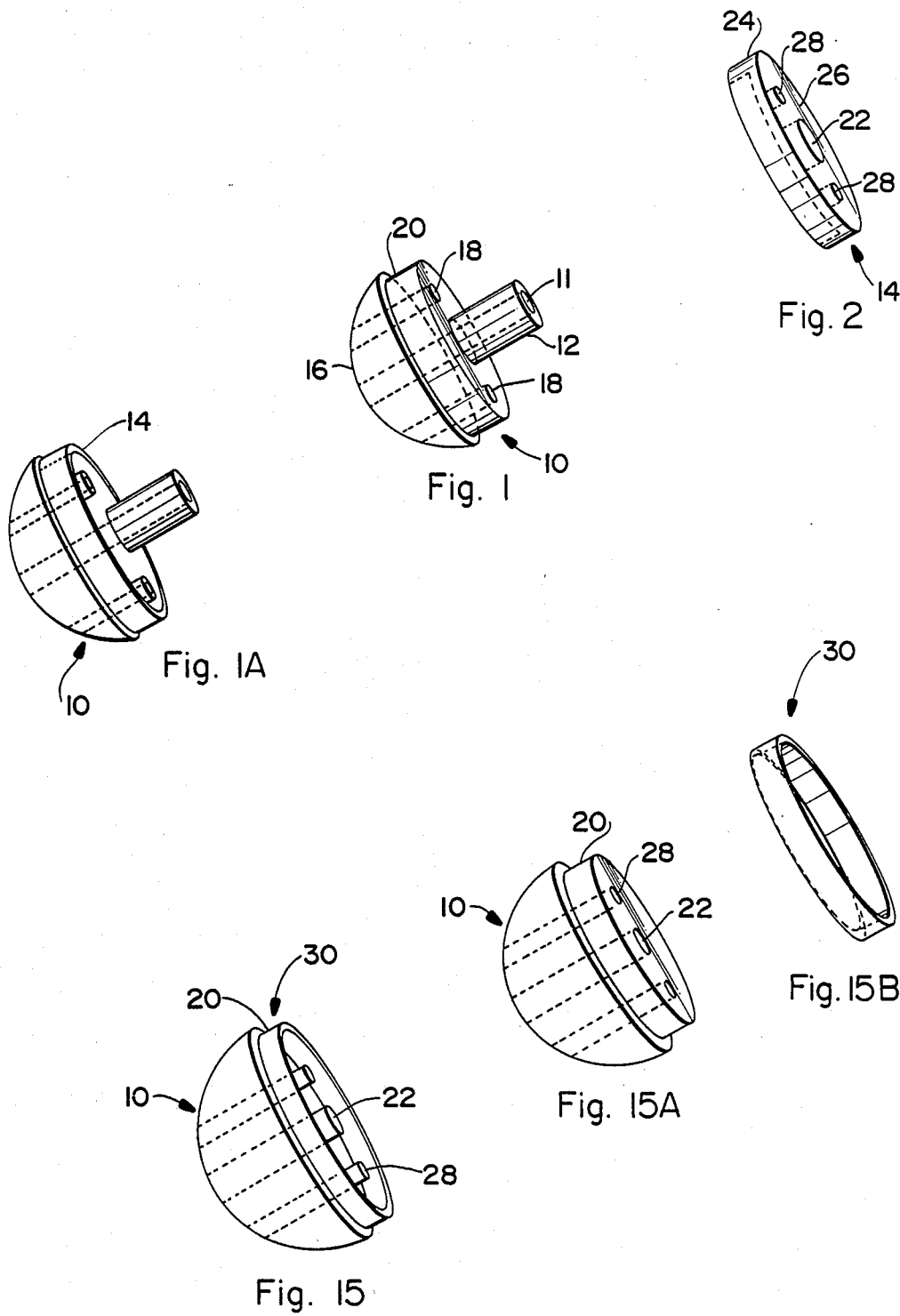

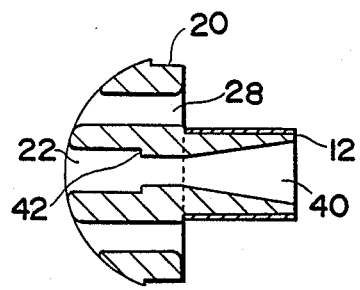
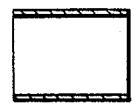
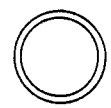
Fig. 16                Fig. 16A
Fig. 16B
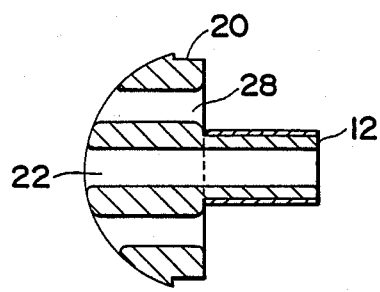
Fig. 17                Fig. 17A
Fig. 17B

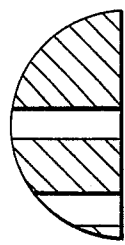
Fig. 18
PRIOR ART
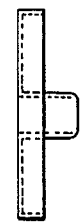
Fig. 19
PRIOR ART
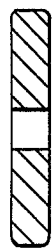
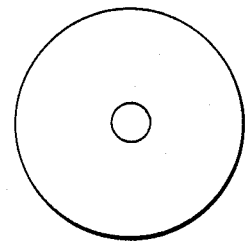
Fig. 20
PRIOR ART
Fig. 20A
PRIOR ART

CATHETER BUTTONS

BACKGROUND

The present invention relates to so called catheter buttons for securing the exterior end or ends of a tube surgically inserted in body tissue, and more particularly to catheter buttons of various shapes and configurations integral with a marking means visible on X-ray images or the like, such as a metallic cap or ring. The buttons may further include a stem portion for facilitating use with such tubes.

Catheter buttons are sometimes known as catheter retainers, as disclosed for example in Edwards U.S. Pat. No. 4,360,025. They have also been called catheter support devices or catheter anchoring devices, as disclosed for example in Jacobs U.S. Pat. No. 4,397,641. In still other embodiments they have been called catheter stabilization pads, as disclosed for example in Kamen U.S. Pat. No. 4,563,177.

Catheter buttons having at least one hole for anchoring a surgical tube have been well known. Additionally, catheter buttons having various geometric shapes are also well known. For example, plastic buttons of spherical, hemispherical or circular, flat disk shapes with an opening for supporting a surgical tube are known. For example, hemispherical buttons are shown in "Brachytherapy Update - 1986," Hilaris, B. S. and Nori, D., Editors, Memorial Sloan-Kettering Cancer Center, New York, Mar. 22, 1986, p. 153. In the case of a circular flat disk, buttons are known to have more than one opening. Such buttons somewhat resemble ordinary shirt buttons. Additionally, metallic marking elements such as flat metallic discs, an flanged discs having an internal stem, the flange and stem of which extend upwardly away from the patient's skin, separate from a button body, have been used in conjunction with a separate non-metallic button body. See again, Hilaris et al., supra.

However, these prior art buttons suffer from many disadvantages. A primary disadvantage is the necessity to handle two small separate pieces, i.e., a button body and a metallic marker, in the surgical theater, especially where many such combinations may be used to secure multiple flexible tubular implants in a single tissue site. Metallic buttons or markers are used because they can be readily identified in X-ray photographs, but it is undesirable to have the metallic markers next to the skin because they cause excessive skin loss due to electron scattering by radiation from radioactive material used in cancer therapy. A further disadvantage of the metallic buttons having stems, is that crimping of the stem to hold the tube within the button is difficult.

BRIEF SUMMARY OF THE INVENTION

Accordingly, it is an object of the present invention to provide new and even more useful catheter buttons.

It is an additional object of this invention to provide a non-metallic catheter button body which integrally includes a metallic marker element.

Still further, it is an object of the present invention to provide a non-metallic catheter button having an integral stem portion.

It is yet another object of the present invention to provide a non-metallic catheter button comprising an integral stem portion, which button is also integral with a metallic marker element.

It is another object of the present invention to provide non-metallic catheter buttons of various geometric shapes.

In accordance with the foregoing objects, the present invention comprises a non-metallic catheter button body having a variety of geometric shapes, having integrally secured therewith a metallic marker element, to anchor a catheter or surgical tube in the body with less pain to the patient while providing an X-ray visible marker, which button substantially reduces the loss of patient's skin from scattered electrons resulting from bombardment by radiation from radioactive material. The non-metallic button body may further include an integral non-metallic stem portion to facilitate the crimping of the stem, anchoring of tubes in the body, and insertion of ribbons of radioactive material therein.

BRIEF DESCRIPTION OF THE DRAWINGS

For a better understanding and further features of the advantageous catheter button system of the resent invention, reference is made to the following drawings of various embodiments of the invention, wherein:

FIG. 1 is a partially schematic isometric view of a partially spheric non-metallic catheter button body of the present invention also including an integral non-metallic stem;

FIG. 1A is a partially schematic isometric view of the non-metallic button body illustrated in FIG. 1 further integral with a metallic marker cap as illustrated in FIG. 2, below;

FIG. 2 is a partially schematic isometric view of a metallic marker cap for use in integral combination with a non-metallic button body in accordance with the present invention;

FIG. 15A is a partially schematic isometric view of an hemispheric non-metallic button body of the present invention, like that illustrated in FIG. 14;

FIG. 15B is a partially schematic isometric view of a metallic ring marking member of the present invention as illustrated in FIGS. 6 and 7;

FIG. 15 is a partially schematic isometric view of an hemispheric non-metallic button body of the present invention integral with a metallic ring marker member;

FIGS. 16 and 17 show partially schematic axial cross-sectional views of metallic crimper/marker sleeves in accordance with the present invention;

FIGS. 16A and 17A show end views of the metallic crimper/marker sleeves of FIGS. 16 and 17, respectively;

FIGS. 16B and 17B show the metallic crimper/marker sleeves of FIGS. 16 and 17, respectively integrally positioned on the integral stem portions of partially spheric non-metallic button bodies according to the present invention;

FIG. 18 shows a prior art non-metallic hemispheric button body not having any external groove;

FIG. 19 shows a prior art metallic marker member having a flat bottom surface and flanged edge and integral metallic stem extending in the same direction from the plane of the flat bottom surface as the flanged edge;

FIGS. 20 and 20A show axial cross-sectional and top views, respectively, of a prior art disk catheter button member.

DETAILED DESCRIPTION OF THE PREFERRED EMBODIMENTS

Figure 5:
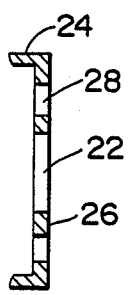
FIG. 5 is an axial cross-sectional view of the metallic marker cap illustrated in FIG. 2.

As shown in FIGS. 1, 1A and 2, one preferred embodiment of the catheter button 10 of the present invention basically comprises a non-metallic hemispherically shaped button body portion 16 having an integral stem portion 12 and an integral metallic marker cap 14, as shown in FIGS. 2 and 5. An opening 11 extends through the stem portion 12 and the hemispherically-shaped button body portion 16. Openings 18 are arranged around the stem 12 and extend from and through the hemispherically-shaped body portion 16. The openings 18 and the opening 11 formed through the stem portion 12 are in a substantially parallel relationship to each other. The hemispherically-shaped body portion 16 further includes an annular exterior groove 20.

The metallic marker cap 14 comprises a flat circular surface 26 having an integral annular flange or lip 24. The cap 14 further includes a central opening 22 and peripheral suture holes 28 disposed around the central opening 22. The opening 22 has a diameter large enough to fit over the stem portion 12. The peripheral suture holes 28 are located to correspond with the suture holes 18 in the button body 10. Furthermore, the annular lip 24 of the cap 14 is formed to fit tightly in the annular groove 20 of the hemispherically-shaped button body portion 16.

Figure 5A:
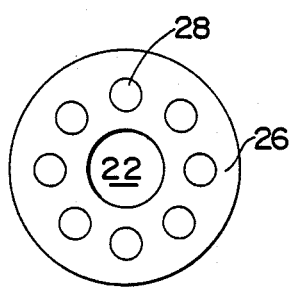
FIGS. 5A-5H, inclusive, illustrate various embodiments of the metallic marker cap previously illustrated in FIGS. 2 and 5, additionally showing a multiplicity of different openings through the top surface of the cap for the purpose of serving as indicia of a specific flexible surgical needle or tube implant.
Figure 5B:
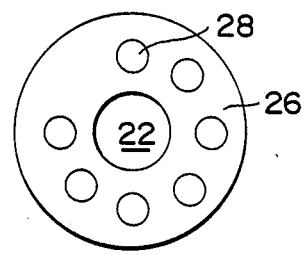
Figure 5C:
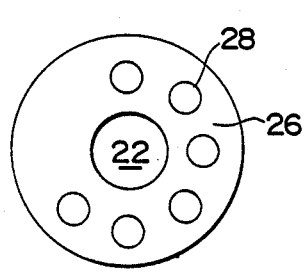
Figure 5D:
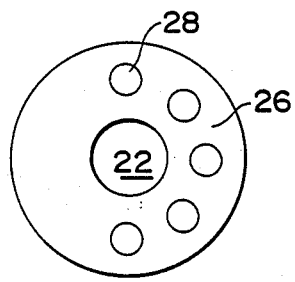
Figure 5E:
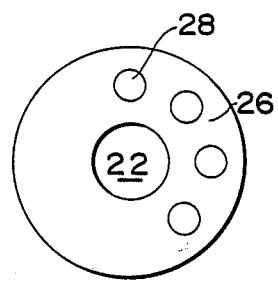
Figure 5F:
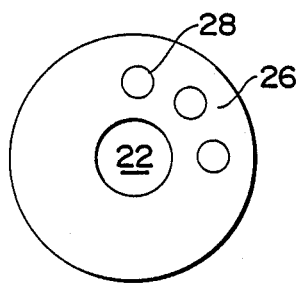
Figure 5G:
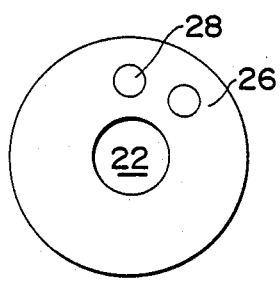
Figure 5H:
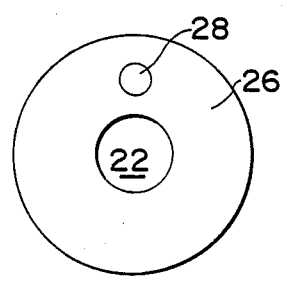

When assembled, the cap portion 14 and button body portion are integrally connected in intimate contact as shown in FIG. 1A. As can be appreciated from FIGS. 5A through 5H, the number of suture holes 28 in the cap 14 is not limited to the number of corresponding openings 18 in the button body. Any number of such holes or openings may be utilized and thereby function as identification marks for a particular implant. Any number of openings may be utilized and arranged in any number of different combinations to serve as distinct identification for any catheter or surgical tube which is secured by such a button. Preferably, the openings 28 are arranged at least at 45° from each other about the outer periphery of the cap around the stem, thereby allowing for as many as eight openings as shown in FIG. 5A. As an example of identification, as shown in FIG. 5D, the cap portion 14 may have five openings, which are arranged 45° from each other. Of course any random or organized pattern of such indicia openings may be used as desired.

In a preferred embodiment, as illustrated in FIGS. 1 and 2, two suture hole openings 18 are arranged on opposite sides of the stem 12. The openings 18 allow the button 10 to be fastened securely in place. Of course, any number of openings may be utilized to fasten the button 10.

The non-metallic button bodies of the present invention typically have diameters of not greater than about 3 cm and the flat disk button bodies typically have thicknesses of not greater than about 0.4 cm. The diameter of the integral metallic marker rings or caps is similarly typically not greater than about 1 cm. A central opening in the button body is designed to fit snugly over the outside circumference of the end of the catheter or surgical implant tube, and the interior of the central opening is preferably stepped down to a diameter approximately equal to the inside diameter of the complimentary catheter or implant tube. The depth of the central opening from the bottom of the non-metallic button body to the desired step down is preferably at least about the length of the outside diameter of the complimentary catheter or surgical implant tube to be secured by the button. This insures that the button body will remain on the exposed end of the catheter or implant tube. Those flexible catheter or implant tubes typically have outside diameters of not greater than about 0.5 cm, and typically have inside diameters of not more than about 0.3 cm, although larger tubes may be used.

Figure 14:
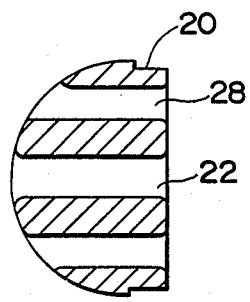
FIG. 14 is a partially schematic axial cross-sectional view of a super-hemispheric non-metallic button body of the present invention also illustrating the circumferential groove for integrally retaining a metallic marker member therewith.
Figure 11:
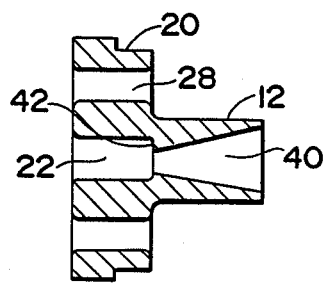
FIG. 11 is a partially schematic axial cross-sectional view of a flat-disk non-metallic button body of the present invention integrally including a non-metallic stem extending coaxially from one face thereof, that stem having the interior funnel-entry shape and the stepped central opening for receiving the end of a flexible surgical needle or tube implant.
Figure 12:
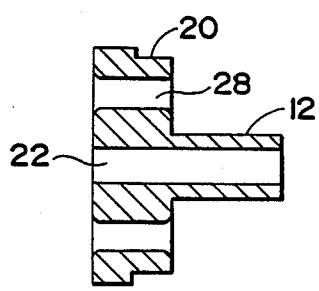
FIG. 12 is a partially schematic axial cross-sectional view of a flat disk-type non-metallic button body of the present invention integrally including a non-metallic stem portion axially extending from one face thereof.
Figure 13:
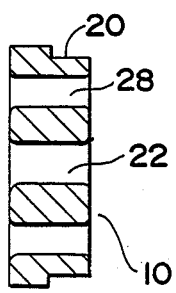
FIG. 13 is a partially schematic axial cross-sectional view of a flat disk-type non-metallic button body of the present invention illustrating the circumferential groove for integrally holding a metallic marking member.
Figure 13A:
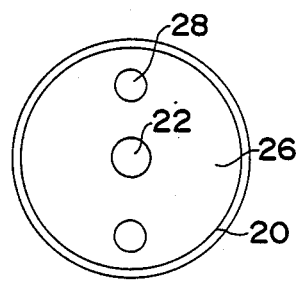
FIG. 13A is a top view of the non-metallic button body illustrated in FIG. 13.

FIGS. 3, 10-13 and 14, respectively, show various embodiments of the advantageous non-metallic button bodies of the present invention. The more elementary forms of such button bodies are illustrated in FIGS. 13 and 14. In FIG. 13 non-metallic button body 10 comprises a flat disk of material having central opening 22 and peripheral suture openings 28 with external groove 20 in the circumference of the button body and intersecting the upper flat face thereof. FIG. 13A shows a top view of the advantageous non-metallic button body of FIG. 13.

Figure 14A:
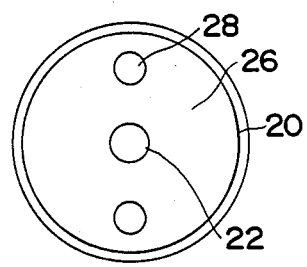
FIG. 14A is a top view of the non-metallic button body of FIG. 14.

FIG. 14 shows a super-hemispherically shaped non-metallic button body otherwise comparable to the flat disk button body illustrated in FIG. 13. This super-hemispherically shaped button body 10 also has central opening 22, peripheral suture holes 28 and circumferential groove 20 which intersects the upper flat surface. FIG. 14A is a top view of the advantageous non-metallic button body of FIG. 14.

Figure 10:
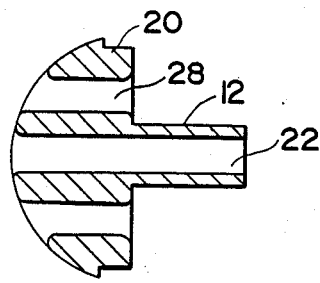
FIG. 10 is a partially schematic axial cross-sectional view of an hemispheric non-metallic button body of the present invention including an integral stem extending away from the top of the button body.
Figure 10A:
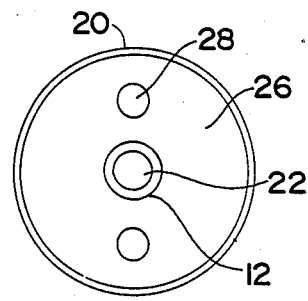
FIG. 10a is a top view of the button body illustrated in FIG. 10.
Figure 12A:
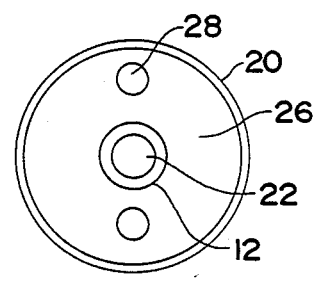
FIG. 12A is a top view of the non-metallic button body illustrated in FIG. 12.

The non-metallic button bodies illustrated in FIGS. 12 and 10, respectively, illustrate a more complex form of the advantageous non-metallic button bodies of the present invention wherein an integral non-metallic stem portion extends coaxially from the top face of the button body 10. It is through that stem portion 12 that central opening 22 extends. The stem portion of the bottom body is typically no longer than the diameter of the bottom body and preferably is long enough to facilitate the crimping functions described herein. One of the functions of the stem portion 12 is to fit over a longer length of the exposed end portion of a catheter or surgical implant tube so that stem 12 may be crimped thereby even more positively gripping the flexible tubular member therein. Additionally, the integral stem catheter buttons of FIGS. 12 and 10, respectively, also include the peripheral circumferential groove 20 which intersects the upper face of the button body 10. FIG. 12A shows a top view of the advantageous non-metallic button body of FIG. 12, and FIG. 10A shows a top view of the advantageous non-metallic button body of FIG. 10.

Figure 3:
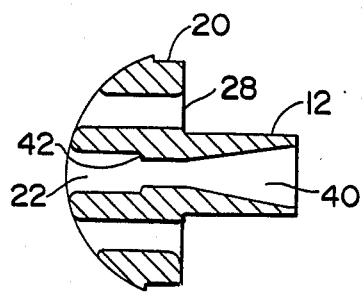
FIG. 3 is a partially schematic axial cross-sectional view of a partial spheric non-metallic button body of the present invention including an integral stem having a funnel entry internal profile, as well as a stepped central opening for receiving the end of a flexible surgical needle or tube.

The non-metallic button bodies illustrated in FIGS. 11 and 3, respectively, illustrate an even more unique button body having an integral stem member 12 extending coaxially from the upper face of the button body wherein the internal surface 40 of stem 12 is funnel-shaped having a larger diameter at the open end of the stem portion 12 which decreases in size toward the central region of the axis of the button body at which point the diameter of the central opening is approximately equal to the inside diameter of a flexible catheter or surgical implant tube with which the button is to be used. Still further, the advantageous button bodies of FIGS. 11 and 3, respectively, show the preferred step-down feature 42 wherein the diameter of the central opening 22 steps down from a diameter substantially the same as the outside diameter of the complimentary catheter or surgical implant tube to the central diameter which, as stated above, is substantially the same as the inside diameter of the complimentary catheter or surgical implant tube. As indicated above, herein, that step down 42 is located at a distance from the bottom of the button body of at least about the length of the outside diameter of the complimentary cathether or surgical implant tube.

Where the inventives button body includes both the step-down feature and an integral stem, the stem may also function to be crimped upon and hold a ribbon of radioactive material in place with the inserted implant tube.

Figure 4:
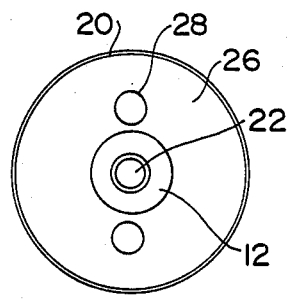
FIG. 4 is a top view of the non-metallic button body illustrated in FIG. 3.
Figure 11A:
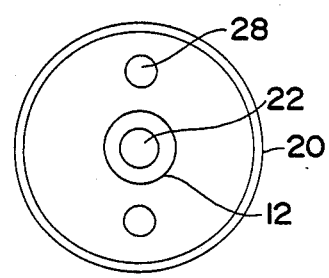
FIG. 11A shows a top view of the non-metallic button body illustrated in FIG. 11.

The other features of the advantageous non-metallic catheter button of FIG. 11 are substantially the same as the features described in conjunction with FIG. 13, while the other features of the button body illustrated in FIG. 3 are substantially the same as the other features illustrated in conjunction with FIG. 14. FIG. 4 is a top view of the advantageous non-metallic button body of FIG. 3, and FIG. 11A is a top view of the advantageous non-metallic button body of FIG. 11.

The advantageous funnel-shaped interior of the stem portion of the non-metallic catheter buttons of FIGS. 3 and 11 respectively, provides means for much more easily threading a ribbon of radioactive treatment seed material into a catheter or surgical implant tube whose exterior end is secured by a catheter button. In the present invention, the open end of the funnel-shaped opening 40 of the stem portion has an inside diameter which is typically some 2 to 4 times the ordinary inside diameter of the catheter or surgical implant tube secured by the button. Thus, it is very substantially more easy to thread a ribbon of radioactive treatment materials into the end of a catheter or implant tube whose exterior end is secured with the advantageous funnel-stemmed catheter button of the present invention. Furthermore, the aforementioned desirable step down feature insures that once such a ribbon enters the central opening of the button body, the end surface of the catheter or surgical implant tube does not impair entry of the ribbon into the catheter or implant tube per se.

Previously, the threading of such ribbons into the external ends of a catheter or implant tube was accomplished by using a portable double-funnel device having funnel cones on each end of an axial passage, which passage itself was no greater than about the inside diameter of the catheter or implant tube into which a ribbon was to be fed. One of the double funnel ends was placed over the external end surface of the end of the catheter or implant tube, while the ribbon sought to be threaded therein was then inserted into the other double funnel cone, and hopefully the technician was able to hold the double funnel device sufficiently still vis-a-vis the exposed end of the catheter or implant tubes for long enough during the attempted threaded process so that threading of the ribbon into the catheter or implant tube per se was actually achieved.

The advantageous button bodies of the present invention having the integral funnel-shaped stem member eliminate the need for the portable double-funnel threading device, and eliminate the frustration of attempting to hold such a device still on the exposed end of a catheter or implant tube. Furthermore, the use of the advantageous button of the present invention is more comfortable for the patient because there is a much diminished tendency for the catheter or implant tube to be moved substantially within the body tissue during the ribbon threading process, whereas the use of the former double funnel device presented a substantial possibility of axial movement of the catheter or implant tube within the patient's tissue.

Figure 6:
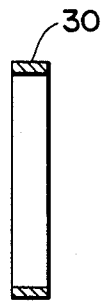
FIG. 6 shows an axial cross-sectional view of a ring-shaped metallic marker for use in integral combination with one of the non-metallic button bodies of the present invention.
Figure 7:
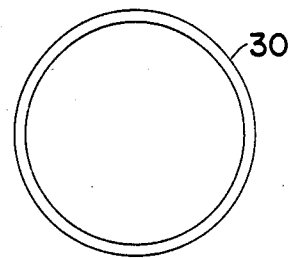
FIG. 7 shows a top view of the metallic ring marker illustrated in FIG. 6.

The metallic marker cap element previously discussed and illustrated in FIGS. 2 and 5, respectively, is but one embodiment of the advantageous metallic marker member portion of the integral button body/- marker combination of the present invention. In FIGS. 6 and 7 a ring-shaped metallic marker member is illustrated. FIG. 6 shows the cylindrical height of the ring and its thickness in axial cross-section, while FIG. 7 is a top view illustrating the circumference, thickness and diameter of such a ring.

Just as the circumferential flange 24 of the metallic marker cap member illustrated in FIGS. 2 and 5 is designed to fit very snugly in circumferential groove 20 in the advantageous non-metallic button bodies of the present invention, thereby integrally connecting such non-metallic button bodies with such metallic marker caps, the ring-type marker 30 is similarly designed to fit snugly in the external peripheral groove 20 on any of the non-metallic button bodies of the present invention. Like the metallic caps discussed earlier herein, the metallic marker ring 30 will be easily visible in any X-ray photgraph of the portion of a patient's body tissue into which a catheter or surgical implant tube has been implanted and has the external end thereof secured by one of the advantageous integral non-metallic button/metallic marker element combinations of the present invention.

Figure 8:
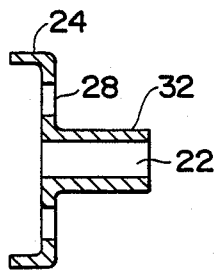
FIG. 8 shows a partially schematic axial cross-sectional view of a flanged cap metallic marker member including an integral metallic stem extending in the direction opposite from the cap flange, which marker is for use in integral combination with one of the non-metallic button bodies of the present invention.
Figure 9:
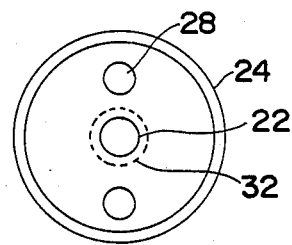
FIG. 9 is a bottom view of the flanged metallic cap with stem illustrated in FIG. 8.

In still a further embodiment, the metallic marker members of the present invention may comprise a cap-like structure as illustrated in FIGS. 8 and 9 wherein the cap-like structure not only includes cylindrical flange 24, but also include an integral metallic stem 32. As with the other marking member embodiments of the present invention, the peripheral flange 24 of the metallic cap-with-stem 32 is designed to fit tightly within peripheral groove 20 on any of the non-metallic marker bodies of the present invention. When such an integral combination is used to secure the end of a catheter or surgical implant tube implanted in body tissue, the metallic stem 32 may be crimped to even more effectively secure the catheter button of the present invention to the exposed end of the catheter or implant tube, or to secure a ribbon of radioactive material in an implant tube, depending upon the particular combination of features present in the button body.

The use of the ring-type metallic marker member 30 is more specifically illustrated in FIG. 15, and in exploded isometric FIGS. 15A and 15B, respectively which show, isometric views of the relationships between an hemispherical non-metallic button body of the present invention and an integral ring-type metallic marker 30 in integral combination as shown in FIG. 15.

It will be appreciated that any of the various ring-type, cap-type or cap-with-stem type metallic marking members of the present invention may be used in integral combination with any of the various flaf disk, disk with stem, or disk with funnel-shaped stem, or disk with stepped-down central opening embodiments of the advantageous non-metallic button members of the present invention. As explained several times above, each of the aforementioned embodiments of the metallic marking member are designed to fit tightly in the peripheral groove 20 on the exterior circumference of the non-metallic button body at the upper surface of that button body.

If desirable to further enhance the integral connection between the button body and metallic marker any suitable adhesive may be used to connect same.

It will be appreciated that any suitable means for integrally connecting the metallic marker with the button body, including the aforementioned snug fitting of a marker disc, ring, cap or flange on the exterior of the button body, fitting of the marker within a peripheral groove on the exterior of the body or either of such fittings together with a suitable adhesive between the same, may be used, and all such means are herein called coupling means.

Together, the integral combination of the non-metallic button body and the metallic marker member provide a very useful new catheter button system. It will be appreciated that the integral button body/marker combination completely eliminates the need for separate handling of two rather small pieces in the surgical theater. This greatly reduces surgery times when many implants are being made to treat difficult and complicated cases. Furthermore, the advantageous marking members of the present invention provide a means for providing unique indicia for each of the exposed ends of a large number of implants in a single tissue site. Still further, as discussed above, the catheter buttons of the present invention with their funnel stem feature provide a quick and accurate means of threading radioactive ribbons into such implant tubes, thereby minimizing unnecessary exposure of patient and doctor or technician during radiological treatments via such implants. Still further, the advantageous step down feature provides a further secure relationship between the button body and the exposed end of an implant tube with which same is used. And still further as explained above herein, the stem portions of the button bodies of the present invention provide still another means for frictionally connecting the button body to the exposed end of an implant tube by crimping the stem onto the exposed end of the implant tube. This array of advantageous features is achieved by the unique integral button body/stem and button body/metallic marker member combinations of the present invention.

Still another feature of the advantageous system of the present invention is illustrated in FIGS. 16 and 17 which show axial cross-sectional views of metallic sleeve members designed to fit integrally over the exterior of the stem portion of the non-metallic button members of the present invention. FIGS. 16A and 17A, respectively, show end views of such metallic sleeve members. FIG. 16B shows a metallic sleeve like that illustrated in FIGS. 16 and 16A in integral combination with a non-metallic button body having an integral stem, such as the button body illustrated in FIG. 3. Similarly, FIG. 17B illustrates the metallic sleeve illustrated in FIGS. 17 and 17A in integral combination with another embodiment of the advantageous non-metallic button bodies of the present invention, like that illustrated in FIG. 10. Not only do such sleeve portions function as metallic marking members in X-ray photographs, but also, such metallic sleeves facilitate secure crimping of the stem portion of the button bodies of the present invention against the exterior of an implant tube whose exterior end is secured by one of the advantageous catheter buttons of the present invention.

The advantages of the system of the present invention become even more clear when the presently claimed invention is compared to the primitive catheter buttons or surgical tube securing devices which were previously known, as discussed at the outset of this specification, some of which are further illustrated in FIGS. 18–20. FIGS. 18, 20 and 20A, respectively illustrate the two forms of catheter buttons typically used prior to the advent of the present invention. FIG. 18 is a simple hemispherical catheter button having a central opening and at least one suture hole, while FIGS. 20 and 20A illustrate a simple flat disk catheter button having at least a central opening and optionally having one or more suture holes. Additionally, FIG. 19 shows a prior art metallic catheter button wherein a peripheral flange as well as a central stem both extend axially from the same side of the flat surface which comprises the bottom of that metallic button. That metallic button was previously used with its flat bottom surface in contact with a patient's skin, an arrangement which further endangered the patient due to electron scattering initiated by radiation from the radioactive materials used to treat the patient in the implant tubes being secured by the buttons. In certain applications, such as that illustrated in the Hilaris reference cited above herein, a separate basic catheter button like that illustrated in FIG. 18 was used along with a separate metallic catheter button like that illustrated in FIG. 19 on the same exterior end of an implant tube to provide X-ray marking as well as a means for securing the external end of the implant tube.

However, none of those prior art devices, or even the occasional combined use of separate prior art devices, in any way suggested the multiplicity of advantages achieved by the presently claimed invention. Furthermore, during the developments which resulted in the presently claimed invention applicant has found that the processes by which the non-metallic button bodies and the metallic marker members, respectively, are made, plays a very substantial role in the successful combination of the two into a truely integral non-metallic body/metallic marker combination. Previously, non-metallic catheter buttons were typically made by punching the button bodies from a sheet of molded plastic material such as nylon, and thereafter drilling the desired holes therein. Applicant has discovered that such procedures are not compatible size-wise and quality-wise with the metallic marking members which are typically made by a different manufacturer at a different site to different tolerances. Applicant has found that it is greatly preferable for the advantageous non-metallic button bodies of the present invention to be specifically molded to provide very accurate control of tolerances so that the flange or ring portion of the metallic marking member and the peripheral groove in the complimentary non-metallic button body are precisely the same size to provide the desired very tight for permanently integrally connecting the two functional portions of the advantageous buttons of the present invention. The manufacture of dies used in the molding process provides the means for carefully controlling the tolerances of the resulting non-metallic button bodies which successfully result in the presently claimed invention.

While the non-metallic button bodies and integral stems of the present invention may be made from known non-metallic materials including ceramics, plastics or polymeric materials such as nylon and acrylics, Zytel 330, a nylon manufactured by E. I. duPont de Nemours & Co., is presently the most preferred material therefor. However, other forms of nylon, and other polymeric material known under the tradename AL-TEMP, manufactured by General Electric Company, and Celcon, a crystalline acetate copolymer based on trioxane, available from Celanese Corporation of America, can be used. It is believed that a wide variety of suitable, relatively inert, manmade polymer materials or other organic or inorganic materials are suitable for use in manufacturing the non-metallic button body portions of the presently claimed invention.

The metallic marker ring 30 or cap 14 is preferably made of stainless steel. However, the cap 14 or ring 30 may comprise aluminum, brass, copper, tungsten, nickel, silver, gold or gold copper alloys, or any other suitable metallic material. Stainless steel and nickel are useful, reasonably priced materials since they do not corrode or rust, and additionally are non-toxic to body tissue and fluids.

While various embodiments of and materials for uses in the presently claimed invention have been described in detail above herein, it will be appreciated by those skilled in the art that certain modifications may be made in those embodiments and their materials, shapes or sizes, which modifications do not depart from the scope or spirit of the invention as defined in the appended claims.

What is claimed is:

1. A catheter button comprising a non-metallic button body portion having a central opening extending therethrough, a metallic marker integral with said body portion, and coupling means for integrally holding the metallic marker on the exterior of the button body.

2. A catheter button of claim 1 wherein said body portion includes an exterior annular groove wherein said marker is integrally held.

3. The catheter button of claim 2, wherein said metallic marker includes a central opening coaxial with the central opening of the button body.

4. The catheter button of claim 1, wherein the button body additionally includes at least one suture hole extending through said body portion and substantially parallel to said central opening.

5. The catheter button of claim 4, wherein said metallic marker includes a central opening and one or more suture holes arranged around said central opening of said metallic marker.

6. The catheter button of claim 5, wherein the metallic member includes a different number of holes than the number of suture holes in said button body.

7. The catheter button of claim 2, wherein said metallic marker is a cap having a circumferential flange integrally held in the exterior annular groove of the button body.

8. The catheter button of claim 2, wherein said metallic marker is a metallic ring integrally held in the exterior annular groove of the button body.

9. The catheter button of claim 7, wherein said metallic cap additionally comprises an integral metallic hollow stem extending coaxially with the central opening of the button body and in the opposite direction from the circumferential flange of the cap.

10. The catheter button of claim 1, further comprising a hollow stem portion integral with and extending from the body portion and through which the central opening also passes.

11. The catheter button of claim 10, wherein the metallic marker is a metallic sleeve integral with and surrounding the stem portion.

12. The catheter button of claim 1, wherein said non-metallic body portion is of substantially hemispherical shape.

13. The catheter button of claim 1, wherein said non-metallic body portion is a flat, disk shape.

14. The catheter button of claim 10, wherein said stem portion has an inner diameter which decreases from the outer end of said stem toward the inner end of said stem, in a conical funnel-like shape.

15. The catheter button of claim 1 wherein the central opening has an initial diameter which is substantially identical to the outside diameter of a surgical tube the end of which is to be secured by said button, and the central opening includes an interior step down at which its internal diameter decreases abruptly to approximately equal the interior diameter of such tube.

16. The catheter button of claim 15 wherein the length of the central opening from the bottom of the button body to the step down is not less than the initial diameter of the central opening.

17. The catheter button of claim 1, wherein the maximum diameter of said button is about 3 cm.

18. The catheter button of claim 1 wherein said non metallic button body comprises nylon.

19. The catheter button of claim 1, wherein said metallic marker comprises a material selected from the group consisting of stainless steel, nickel, tungsten, aluminum, brass, copper, silver, gold and gold copper alloy.

20. The catheter button of claim 1, wherein said non-metallic body portion and said metallic marker are integrally fastened together with adhesive.

21. A catheter button comprising a non-metallic body button body and a hollow, substantially nonelastic stem portion extending from and integral with said button body portion wherein a central opening extends through said body portion and said hollow stem, said stem portion having an outer continuous wall structure and an inner diameter which decreases from the outer end of said stem toward the inner end of said stem, in a conical, funnel-like shape.

22. The catheter button of claim 21, wherein the central opening has an initial diameter which is substantially identical to the outside diameter of a surgical tube the end of which is to be secured by said button, and the central opening includes an interior step down at which its internal diameter decreases abruptly to approximately equal the interior diameter of such tube.

23. The catheter button of claim 22, wherein the length of the central opening from the bottom of the button body to the step down is not less than the initial diameter of the central opening.

24. The catheter button of claim 21, wherein the maximum diameter of said button is about 3 cm.

25. The catheter button of claim 21, wherein said non metallic body portion is of substantially hemispherical shape.

26. The catheter button of claim 21, wherein said non metallic body portion is of a flat, disk shape.

27. The catheter button of claim 21 wherein said non metallic button body and stem comprise nylon.

28. The catheter button of claim 21 wherein the button body additionally includes at least one suture hole extending through said body portion substantially parallel to said central opening.

29. A catheter button comprising a non-metallic button body portion, a hollow stem portion extending from and integral with said button body portion and a central opening extending through said body portion and said hollow stem, wherein the central opening has an initial diameter which is substantially identical to the outside diameter of a surgical tube, the end of which is to be secured by said button, and the central opening includes an interior step down at which its internal diameter decreases abruptly to approximately equal the interior diameter of such tube.

30. The catheter button of claim 29, further comprising a metallic marker integral with said body portion.

31. The catheter button of claim 30, wherein said body portion includes an exterior annular groove wherein said marker is integrally held.

32. The catheter button of claim 31, wherein said metallic marker includes a central opening coaxial with the central opening of the button body.

33. The catheter button of claim 30, wherein the button body additionally includes at least one suture hole extending through said body portion substantially parallel to said central opening.

34. The catheter button of claim 33, wherein said metallic marker includes a central opening and one or more suture hole arranged around said central opening of said metallic marker.

35. The catheter button of claim 34, wherein the metallic member includes a different number of holes than the number of suture holes in said button body.

36. The catheter button of claim 31, wherein said metallic marker is a cap having a circumferential flange integrally held in the exterior annular groove of the button body.

37. The catheter button of claim 31, wherein said metallic marker is a metallic ring integrally held in the exterior annular groove of the button body.

38. The catheter button of claim 36, wherein said metallic cap additionally comprises an integral metallic hollow stem extending coaxially with the central opening of the button body and in the opposite direction from the circumferential flange of the cap.

39. The catheter button of claim 30, wherein the metallic marker is a metallic sleeve integral with and surrounding the stem portion.

40. The catheter button of claim 29, wherein the button body portion is of substantially hemispherical shape.

41. The catheter button of claim 29, wherein the button body portion is of a flat, disk shape.

42. The catheter button of claim 30, wherein said metallic marker comprises a material selected from the group consisting of stainless steel, nickel, tungsten, aluminum, brass, copper, silver, gold and gold copper alloy.

43. The catheter button of claim 30, wherein said non-metallic body portion and said metallic marker integrally fastened together with adhesive.

* * * * *